United States Patent
Geloven et al.

(10) Patent No.: US 6,277,267 B1
(45) Date of Patent: Aug. 21, 2001

(54) GAS SENSOR

(75) Inventors: Peter Van Geloven, Nieuwerkerken; Silvia Lenaerts, Kuringen; Patrick van de Voorde, Loppem, all of (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 09/473,833

(22) Filed: Jan. 3, 2000

Related U.S. Application Data

(62) Division of application No. 09/312,049, filed on May 14, 1999, now abandoned, which is a continuation of application No. PCT/EP98/06036, filed on Sep. 14, 1998.

(30) Foreign Application Priority Data

Sep. 15, 1997 (DE) ............................................. 197 40 500
Dec. 20, 1997 (DE) ............................................. 197 57 112

(51) Int. Cl.[7] .................................................. G01N 27/407

(52) U.S. Cl. .......................... 205/781; 204/424; 204/425; 204/427; 205/784.5; 205/785

(58) Field of Search ..................................... 204/421–429; 205/781, 783.5, 784, 784.5, 785

(56) References Cited

U.S. PATENT DOCUMENTS

| | | |
|---|---|---|
| 3,514,377 | 5/1970 | Spacil et al. . |
| 4,101,403 | 7/1978 | Kita et al. . |
| 4,145,272 | 3/1979 | Nakamura et al. . |
| 4,172,247 | 10/1979 | Ikeura . |
| 4,300,991 | 11/1981 | Chiba et al. . |
| 4,402,820 | 9/1983 | Sano et al. . |
| 4,416,763 | 11/1983 | Fujishiro . |
| 4,427,525 | 1/1984 | Ching et al. . |
| 4,476,008 | 10/1984 | Sano et al. . |
| 4,487,680 | 12/1984 | Logothetis et al. . |
| 4,502,939 | 3/1985 | Holfelder et al. . |

(List continued on next page.)

FOREIGN PATENT DOCUMENTS

| | | |
|---|---|---|
| 4109516C2 | 8/1992 | (DE) . |
| 4225775A1 | 2/1994 | (DE) . |
| 19534918A1 | 1/1997 | (DE) . |
| 0335666A3 | 10/1989 | (EP) . |
| WO 95/30146 | 11/1995 | (WO) . |
| WO 96/17242 | 6/1996 | (WO) . |

OTHER PUBLICATIONS

Kato, Nobuhide et al., "Thick Film ZrO2 $NO_x$ Sensor", Soc. Automot. Eng., (SAE Paper 960334), 137–142, SP1996, SP–1149 (Electronic Engine Controls 1996).

Nakanouchi, Yukio et al. "New Type of $NO_x$ Sensors for Automobiles", Soc. Automot. Eng., (SAE Paper 961130), 157–164 (1996).

*Primary Examiner*—T. Tung
(74) *Attorney, Agent, or Firm*—Akin, Gump, Strauss, Hauer & Feld, L.L.P.

(57) ABSTRACT

A method for measurement of nitrogen oxides using a gas sensor. To reliably measure nitrogen oxides, the sensor has a reference electrode representing a constant oxygen partial pressure, at least two electrode pairs, with common a electrode associated with each pair of electrodes, and solid electrolytes arranged between the two electrodes of an electrode pair directly at the electrodes. The solid electrolyte between a first electrode pair is gas-permeable, while the solid electrolyte between a second electrode pair is gastight, whereby the second electrode pair is adapated for potentiometric or amperometric measurement of nitrogen oxides, and the first electrode pair is adapted for application of a current or a voltage to pump oxygen. The second electrode of the second electrode pair is constructed as a reference electrode on the reference gas side of the solid electrolyte of the second electrode pair. The sensor also has electrical leads for connection and for take-away of electric measurement signals.

6 Claims, 3 Drawing Sheets

U.S. PATENT DOCUMENTS

| | | |
|---|---|---|
| 4,510,036 | 4/1985 | Takeuchi et al. . |
| 4,578,172 | 3/1986 | Yamada et al. . |
| 4,828,673 | 5/1989 | Maeda . |
| 4,908,119 | 3/1990 | Saito et al. . |
| 5,397,442 | 3/1995 | Wachsman . |
| 5,460,711 | 10/1995 | Riegel et al. . |
| 5,482,609 | 1/1996 | Kobayashi et al. . |
| 5,672,811 | 9/1997 | Kato et al. . |

US 6,277,267 B1

GAS SENSOR

CROSS REFERENCE TO RELATED APPLICATION

This application is a division of application Ser. No. 09/312,049 filed May 14, 1999, now abandoned, entitled GAS SENSOR which is a continuation of International Application PCT/EP98/06036, filed Sep. 14, 1998, the disclosure of which is incorporated herein by reference.

BACKGROUND OF THE INVENTION

The invention relates to method for measuring oxygen and/or the air/fuel ratio lambda and nitrogen oxides in gas mixture. The sensor has a reference electrode representing a constant oxygen partial pressure, at least two electrode pairs, wherein two electrode pairs each have a common electrode associated therewith The gas sensors also have solid electrolytes arranged between the two electrodes of each electrode pair directly at the electrodes and electrical leads for connection and for take-away of electrical measurement signals.

A gas sensor of a this type is known, e.g., from German published patent application DE 195 34 918 A1. The sensor therein has two electrodes constructed as mutually engaging comb structures (see FIG. 1), which are arranged on the side of the solid electrolyte facing he gas being measured (hereinafter "measurement gas"), and a reference electrode is provided opposite thereto on the reference air side. That invention is directed mainly to a reliable seal to ensure that no effects are exerted on the operation and performance of the two electrodes (sensor contacts) provided on the measurement gas side of the solid electrolyte. This construction makes possible a voltammetric measurement of two gas components in a gas mixture.

In addition, a gas sensor of the generic type is known from German published patent application DE 36 10 366 A1, in which a plurality of electrochemical measuring cells are arranged on a tubular support This device allows only gaseous pollutants to be measured (not oxygen). The evaluation of the measurement signals takes place based on the characteristics of the pollutant concentrations.

Furthermore, a gas sensor of this type is known from German Patent DE 41 09 516 C2. In this device, the solid electrolyte is constructed in the shape of a platelet, on one side of which an electrode is applied which functions as a reference electrode, and on the opposite side of which at least two measuring electrodes are applied, which interact with various components of a gas mixture. The platelet-shaped sensor is built into a housing, which is then to be installed as a gas probe in the exhaust gas duct of a motor vehicle, more specifically perpendicular to the flow direction of the exhaust gas.

This probe functions without a reference gas, which is required for obtaining an electrode potential independent of the environment. However, such electrodes are not stable with respect to their electrochemical potential, especially when the mixture composition changes from lean to rich. In addition, with configurations of the sensor design which are not rotationally symmetric, it is very hard to realize a stable and uniform temperature distribution over the entire surface.

The nitrogen oxide ($NO_x$) measuring electrode and the negative pumping electrode are two electrodes, which are arranged locally separated from each other. It is difficult to establish a low oxygen concentration at the nitrogen oxide measuring electrode, since more oxygen is always present which cannot be removed by the pumping electrode, because it does not reach this pumping electrode.

Similar gas sensors, relatively complicated in construction, are also known from German published patent application DE 42 25 775 A1. In the sensors described there, a constant voltage is applied respectively between a reference electrode and a measuring electrode, as well as between the measuring electrode and a counter-electrode, and the current exiting from the counter-electrode is measured as a function of the nitrogen oxide concentration.

SUMMARY OF THE INVENTION

In view of the above, an object of the present invention is to provide a method for measurement of nitrogen oxides using a gas sensor with which at least two gaseous components can be reliably detected simultaneously over a wide range of gas mixtures, and which also ensures a stable reference signal with the aid of ambient air, which additionally and, if necessary, allows the influence of the oxygen concentration by adding or removing oxygen at the respective measuring electrodes.

According to the invention, these objectives are achieved with the solid electrolyte between a first electrode pair being gas-permeable and the solid electrolyte between a second electrode pair being gas-tight, wherein the second electrode pair is provided for potentiometric or amperometric measurement of the nitrogen oxide concentration, the first electrode pair is constructed for applying a current or a voltage for pumping oxygen, the common electrode forms the cathode of the first electrode pair, and the second electrode of the second electrode pair is constructed as a reference electrode on the reference gas side of the solid electrolytes of the second electrode pair. Advantageous amplifications of the invention and uses of the gas sensor according to the invention are described below and set forth in the dependent claims.

Advantageously the solid electrolyte, generally provided as a solid electrolyte body of virtually any desired shape, is constructed as a small tube closed at one end, which has on its inner wall a reference electrode, positioned as close as possible to the closed end, and a plurality of electrodes arranged on the outer side, exposed to the measurement gas. The solid electrolyte consists, e.g., of partially or filly stabilized $ZrO_2$ or of $CeO_2$. The arrangement of at least two independent measuring electrodes on the solid electrolyte guarantees the simultaneous detection of at least two measurement signals which correspond to at least two different gas components. Since a tubular solid electrolyte with a circular cross-section is used, the disturbances at an installation point perpendicular to the exhaust gas flow are thereby minimized, so that the measurement gas flows around the sensor in a relatively uniform manner. Accordingly, the gas components being measured arrive at the measuring electrodes practically without a delay, and the disturbing turbulence is avoided.

If the gas sensor is used at temperatures below 400° C., it is advantageous to provide the sensor with a heating element The heating element for this purpose can be applied as a heating conductor, likewise on the outer side of the solid electrolyte, wherein, however, in order to avoid a short circuit, an electrically insulating layer is arranged between the heating conductor and the solid electrolyte.

Expediently, one of the electrodes used as a measuring electrode on the outer side of the solid electrolyte tube, which is closed at one end, is made of a catalytically active material and is consequently particularly suited for the potentiometric oxygen measurement according to the principle of a Nernst probe. In contrast, the second measuring electrode is made of a catalytically inactive material.

As materials for at least one of the electrodes, platinum or platinum alloys have proven satisfactory. Furthermore, rhodium, palladium, iridium, or their alloys are also suitable as (also in some cases catalytically active) electrode materials. Among the (catalytically inactive) materials, which should be used for the second measuring electrode, gold and gold alloys, as well as metal oxides have proven satisfactory. The catalytically inactive metal oxides are exemplified by mixed-conductivity perovskite compounds. Other simple metal oxides can also be used as (non-catalytic) electrode materials, e.g., $SnO_2$, $TiO_2$, $V_2O_5$, $Fe_2O_3$, NiO, ZnO, $Sb_2O_3$, $Cr_2O_3$, CuO, or $MnO_2$. By varying the composition of the measuring electrodes, different gaseous components can be brought for interaction with the electrodes.

In using the gas sensor in a method for nitrogen oxide measurement, a voltage or current is applied to a pair of electrodes, which consist of at least two measuring electrodes or of one of two measuring electrodes and a reference electrode. A negative potential is applied at the commonly used electrode. This electrode is referred to as the "pumping electrode," i.e., it pumps off oxygen, so that the measurement of nitrogen oxides at the respective other electrode pair can be carried out at minimized oxygen concentration. If the construction of the sensor is expanded to the extent that a cascade of electrodes is provided, which are positioned one over the other but are separated from each other by porous solid electrolyte diffusion layers lying therebetween, the output capacity of the oxygen pump can be increased, as required. The electrode with positive potential in the electrode pair, to which a voltage or current is applied, can be made of a catalytically active or catalytically inactive material, as further cited above. If a catalytically active material is chosen, it is possible that certain gaseous components may react or decompose at this electrode, and thus will not reach the pumping electrode. If nitrogen oxide ($NO_x$) is decomposed in this manner into $N_2$ and $O_2$, this is disadvantageous for the detection of $NO_x$. For this reason, it can be advantageous in a nitrogen oxide sensor to form the positive electrode from a catalytically inactive material.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
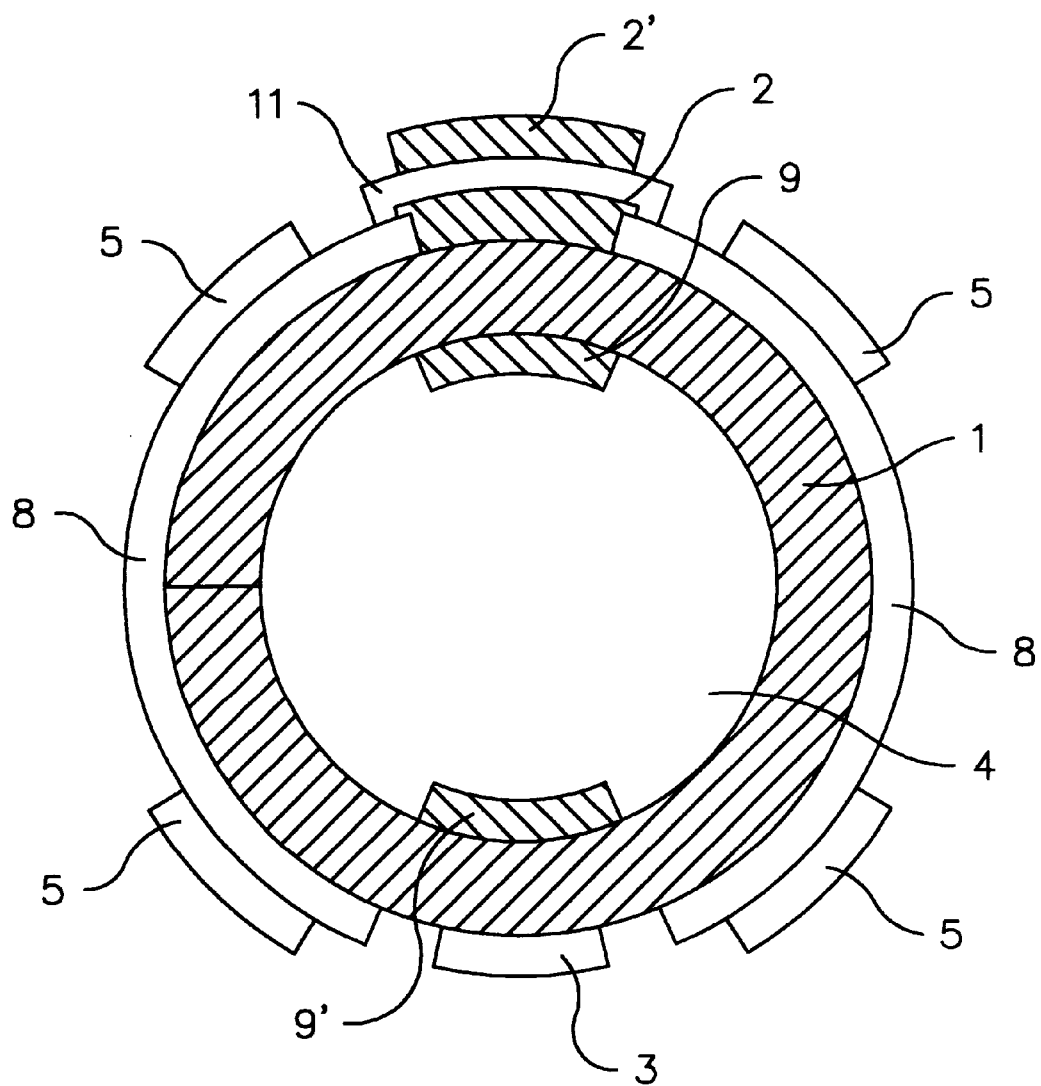
FIG. 1 is a sectional view through a tubular gas sensor according to the preferred embodiment of the present invention for amperometric or potentiometric nitrogen oxide determination, as well as for potentiometric hydrocarbon determination.

FIG. 1 shows one embodiment of the invention. A catalytically inactive electrode 3 of a perovskite material is arranged on a tubular solid electrolyte 1 of $ZrO_2$, and the reference electrode 9' is provided opposite thereto in a reference air canal 4. Further, an insulating layer 8 of $Al_2O_3$ is arranged on the outer side of the solid electrolyte 1 ($ZrO_2$ tube), and a heating element 5 is installed on this layer on the outer side of the solid electrolyte 1 for rapid heating of this gas sensor. A catalytically inactive electrode 3 of a perovskite material and a catalytically active electrode 2 of platinum are applied on the outer side of the gas-tight solid electrolyte 1. The latter electrode is covered with a qurous solid electrolyte layer of $ZrO_2$, which can be constructed to allow diffusion.

A reference electrode 9, 9' (or counter-electrodes 9') is provided in the interior of the tube 1 opposite the two measuring electrodes 2, 3, respectively. According to this embodiment, the potentiometric measurement of hydrocarbons is carried out by means of the measuring electrode 3 and the reference electrode 9'. Additionally, one further measuring electrode 2' is provided over the solid electrolyte layer 11. In this case, the solid electrolyte layer 11 is constructed as a gas-permeable solid electrolyte, so that between the two measuring electrodes, by applying an electrical voltage between the negative electrode 2 and the positive electrode 2', the oxygen from the measurement gas, which reaches the electrode 2 through the solid electrolyte layer 11, is transformed into ions and pumped toward the electrode 2', and there leaves the sensor as molecular oxygen. By this pumping effect at the first electrode pair 2, 2' oxygen is pumped away from the measuring electrode 2, so that at the triple point of this electrode 2, at which nitrogen oxide should be measured, a low oxygen concentration prevails.

One of the advantages of this invention lies in the fact that the electrode 2 of the pairs of electrodes 2, 2' (the pumping electrode pair) and 2, 9 (the measuring electrode pair) is a common electrode, and also in the fact that the low oxygen concentration occurs exactly where it is needed, namely at the nitrogen oxide measuring electrode 2. The nitrogen oxide measurement is carried out potentiometrically or amperometrically by means of the electrodes 2, 9. The solid electrolyte 1 is, for example, mounted in a housing in a manner well known to those skilled in the art, wherein the individual layers and electrodes can be electrically contacted, for example at an end of the solid electrolyte 1 in a likewise known manner.

Figure 2:
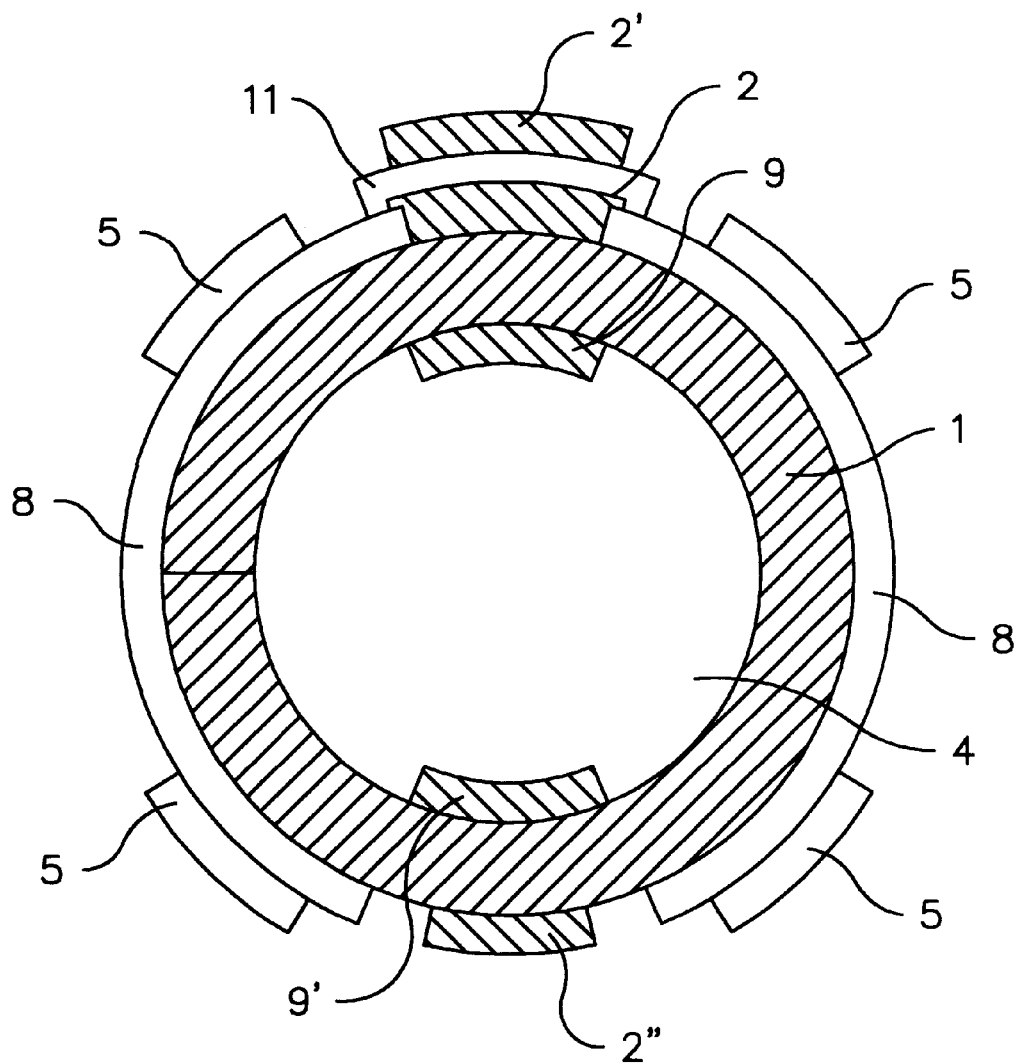
FIG. 2 is a sectional view through a tubular gas sensor according to the invention for potentiometric oxygen or lambda determination and for amperometric nitrogen oxide determination.

In FIG. 2 the catalytically inactive measuring electrode 3 is replaced by a catalytically active measuring electrode 2". The potentiometric lambda or oxygen measurement takes place here via the measuring electrode 2' with respect to the reference electrode 9'. Optionally, the measurement can also be carried out amperometrically by means of the electric current flowing through the electrode pair 2, 2' or 2, 9. The nitrogen oxide determination follows the amperometric or potentiometric principle analogous to the example according to FIG. 1.

Figure 3:
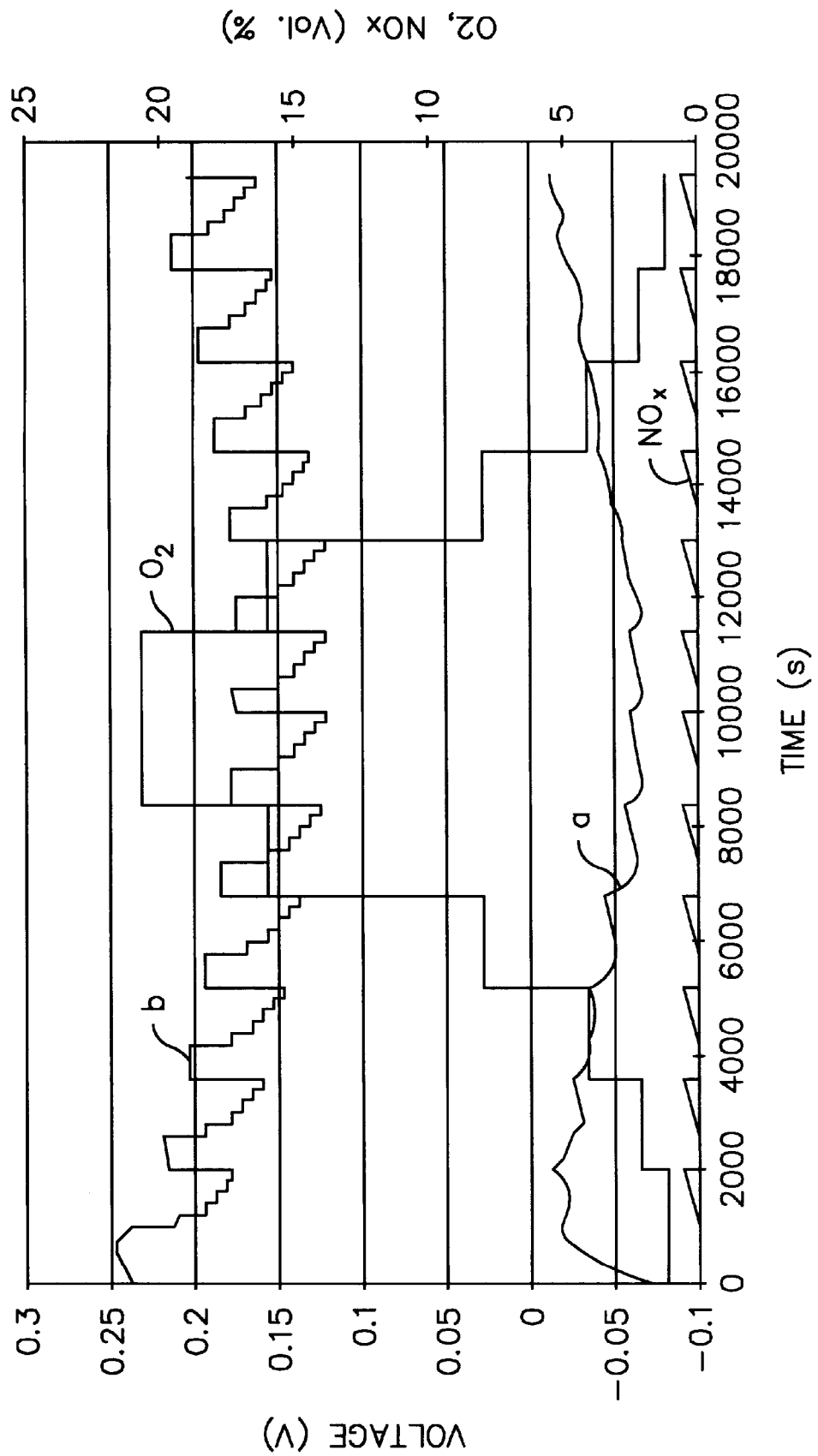
FIG. 3 is a set of characteristic curves for $NO_x$ and oxygen from a sensor according to FIG. 2.

FIG. 3 shows characteristic curves of a sensor according to FIG. 2. The potentiometric measurement principle is used here for both the oxygen and $NO_x$ measurements. The voltage U in volts is plotted on the left-hand y-axis, and the $O_2$ and $NO_x$ concentrations are plotted in vol. % on the right-hand y-axis, all as a function of time. The concentrations of oxygen and nitrogen oxide are determined by the potentiometric measuring principle. Curve "a" represents the potentiometric oxygen signal, measured at the electrode pair 2", 9', and curve "b" represents the combined electric voltage from the oxygen and nitrogen oxide concentration, measured at the electrode pair 2, 9. Based on the data of curves "a" and "b", the nitrogen oxide concentration can be determined.

The signal from the oxygen and/or lambda sensor, if installed downstream of a catalyst, can be used for the calibration of a lambda sensor installed upstream of the catalyst. The measurement signal from the oxygen and/or lambda sensor can also be used for a correction of a nitrogen oxide sensor or for a calibration of the nitrogen oxide sensor.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A method for the measurement of nitrogen oxides using a gas sensor comprising, at least one reference electrode (9; 9') for representing a constant oxygen partial pressure, at least two electrode pairs (9, 2; 2, 2'), at least two of the electrode pairs (9, 2 and 2, 2') having a common measuring electrode (2), and a solid electrolyte (1; 11) being arranged between electrodes of the electrode pairs (9, 2; 2, 2') and in contact with the electrodes, wherein the solid electrolyte (11) between a first electrode pair (2, 2') is gas-permeable, and a second solid electrolyte (1) between a second electrode pair (9, 2) is gas-tight, the second electrode pair (9, 2) being adapted for one of a potentiometric measurement and an amperometric measurement of a concentration of the nitrogen oxides, and the first electrode pair (2, 2') being constructed for application of one of a voltage and a current for at least one of pumping and measuring oxygen, and wherein the common measuring electrode (2) forms a cathode of the first electrode pair (2, 2'), and a second electrode (9) of the second electrode pair (9, 2) is constructed as one of the at least one reference electrodes on a reference gas side (4) of the second solid electrolyte (1), and further comprising electrical leads for connection and for transmission of electric measurement signals, the method comprising the steps of:

forming an electrode pair (2', 2; 2, 9) from one of the electrodes (9; 2') of the gas sensor and the common measuring electrode (2) by application of one of a voltage and a current, wherein the common measuring electrode (2) has a negative potential, such that oxygen in the gas being measured is pumped away from the common measuring electrode (2), and measuring the nitrogen oxides with the second electrode pair (9, 2).

2. The method of claim 1 wherein at least one of the voltages and currents is applied continuously.

3. The method of claim 1 wherein at least one of the voltages and currents is applied using pulses.

4. The method of claim 1 wherein the gas sensor is arranged downstream of a catalyst, and at least one of an oxygen pumping and oxygen measuring signal from the gas sensor is used to calibrate an oxygen sensor installed upstream of the gas sensor.

5. The method of claim 1 wherein one of a signal from an oxygen sensor and at least one of an oxygen pumping and oxygen measuring signal from the gas sensor is used to correct a nitrogen oxide signal of the gas sensor.

6. The method of claim 1 wherein one of a signal from an oxygen sensor and at least one of an oxygen pumping and oxygen measuring signal from the gas sensor is used to calibrate a nitrogen oxide signal of the gas sensor.

* * * * *